US006414320B1

(12) United States Patent
Ishikawa et al.

(10) Patent No.: US 6,414,320 B1
(45) Date of Patent: Jul. 2, 2002

(54) COMPOSITION ANALYSIS BY SCANNING FEMTOSECOND LASER ULTRAPROBING (CASFLU).

(75) Inventors: Muriel Y. Ishikawa, Livermore; Lowell L. Wood, Simi Valley; E. Michael Campbell, Danveille; Brent C. Stuart; Michael D. Perry, both of Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/563,122

(22) Filed: May 2, 2000

Related U.S. Application Data

(60) Provisional application No. 60/132,246, filed on May 3, 1999.

(51) Int. Cl.[7] .......................... B23K 26/00; B23K 26/32
(52) U.S. Cl. ................ 250/425; 250/423 R; 250/492.1; 250/251; 250/288; 219/121.6; 219/121.68; 216/65; 606/11
(58) Field of Search ............................. 250/425, 423 R, 250/492.1, 251, 288; 219/121.6, 121.68; 216/65; 606/11

(56) References Cited

U.S. PATENT DOCUMENTS 5,720,894 A  2/1998 Neev et al. ................... 216/65
6,156,030 A  * 12/2000 Neev ........................... 606/10
6,333,485 B1 * 12/2001 Haight et al. .......... 219/121.68

FOREIGN PATENT DOCUMENTS

WO   WO 98/55035   12/1998

OTHER PUBLICATIONS

Database Inspec 'Online, Institute of Electrical Engineers, Stevenage, Banerjee S. et al: "Highly Charged Ion Production by Intense, Ultrashore Laser Pulse Excitation of Solids" Database accession No. 6413618; XP–000911864.

* cited by examiner

*Primary Examiner*—Bruce Anderson
*Assistant Examiner*—Nikita Wells
(74) *Attorney, Agent, or Firm*—John P. Wooldridge; Alan H. Thompson

(57) ABSTRACT

The composition analysis by scanning femtosecond ultraprobing (CASFLU) technology scans a focused train of extremely short-duration, very intense laser pulses across a sample. The partially-ionized plasma ablated by each pulse is spectrometrically analyzed in real time, determining the ablated material's composition. The steering of the scanned beam thus is computer directed to either continue ablative material-removal at the same site or to successively remove nearby material for the same type of composition analysis. This invention has utility in high-speed chemical-elemental, molecular-fragment and isotopic analyses of the microstructure composition of complex objects, e.g., the oxygen isotopic compositions of large populations of single osteons in bone.

24 Claims, 4 Drawing Sheets

COMPOSITION ANALYSIS BY SCANNING FEMTOSECOND LASER ULTRAPROBING (CASFLU).

This application claims priority to provisional patent application serial No. 60/132,246, filed May 3, 1999, titled "Composition Analysis by Scanning Femtosecond Laser Ultraprobing (CASFLU)."

The U.S. Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to composition analysis, and more specifically, it relate) to multi-dimensional composition analysis of objects using sequences of ultrashort laser pulses to ablatively present trains of small mass-packets for examination by a variety of analytic instruments.

2. Description of Related Art

The surface region of a sample may be analyzed by removing surface material and analyzing that removed material by mass spectrometry. The step of removing sample material may be accomplished in a number of ways generally involving the input of heat, the transfer of momentum or an electronic excitation. For example, in a laser microprobe an intense focused laser probe ablates sample material and provides ions for analysis, as reviewed by R. J. Cotter and J. C. Tabet in American Laboratory 1984, 16(4), pages 86 to 99. Laser probes of low power density are particularly advantageous in the analysis of bio-organic molecules as reported by M. A. Posthumus et al in Analytical Chemistry 1978, 50(7), pages 985 to 991. Other widely used techniques include secondary ion mass spectrometry (SIMS) and fast atom bombardment (FAB) mass spectrometry wherein a beam of ions or atoms sputters material from a sample, as reviewed by A. Benninghoven et al. in SIMS, volume 86 of Chemical Analysis, 1987 published by John Wiley & Sons.

Alternatively, electrons or photons may be employed for stimulating desorption from adsorbed layers or from the outermost atomic layers of a sample as described by J. A. Kelber and M. L. Knotek in the Springer Series in Surface Science, 1985, volume 4, pages 182 to 187. Thus there is available a range of techniques for removing and subsequently analyzing material from a range of depths, from the outer monolayer down to several tens or hundreds of microns. Moreover these techniques may be combined with an eroding technique such as ion milling to investigate essentially any desired depth.

The above-mentioned techniques generally produce more neutral particles than ions and that neutral emission is not subject to discriminating influences that can make ionic emission unrepresentative of the surface composition. It has long been recognized that it would be advantageous to provide means for post-ionizing the neutrals to facilitate their analysis by mass spectrometry, and suitable techniques have been reviewed by W. Reuter in the Springer Series in Chemical Physics 1986, 44 pages 94 to 102 and by A. Benninghoven et al (op cit 1987) pages 937 to 949. Post-ionization by an electron beam is described by R. E. Honig in the Journal of Applied Physics 1958, 29(3), pages 549 to 555; by A. J. Smith in the Journal of Applied Physics 1963, 34, pages 2489 to 2490; by D. Lipinsky et al in the Journal of Vacuum Science and Technology, 1985, A3, pages 2007 to 2017; and by I. R. M. Wardell in U.S. Pat. No. 3,660,655. A disadvantage of electron beam post-ionization is that it provides a low ion yield, given by W. Reuter as $10^{-9}$ ions per atom. Post-ionization by an electron gas or by a plasma has also been reported with ion yields according to W. Reuter of $10^{-9}$ and $10^{-7}$ respectively, whereas more satisfactory yields in the region of $10^{-2}$ to $10^{-4}$ are reported for by various laser beam post-ionization techniques. Prior to this laser work, photoionization by light from spark or other discharge lamps had been employed in the analysis of gaseous and thermally evaporable samples as reported for example by W. Genuit and J. J. Boon in the Journal of Analytical and Applied Pyrolysis 1985, 8, pages 25 to 40; by M. E. Akopyan et al in in Instrum Exp Tech 1972, 15(2), pages 1481 to 1482; in U.S. Pat. Nos. 4,521,054, 4,028,617 and 4,476,392; and as reviewed by N. W. Reid in the International Journal of Mass Spectrometry and Ion Physics 1971, 6, pages 1 to 31. Such photoionization mass spectrometry is generally compared unfavorably with electron impact ionization mass spectrometry because of its low ion yield, as described by W. Poschenrieder and P. Warneck in the Journal of Applied Physics 1966, 37(7), pages 2812 to 2820. D. F. Hunt in The International Journal of Mass Spectrometry and Ion Physics 1982, 45, pages 111 to 123 points out that lasers are required to provide a sufficiently high photon flux as exemplified by the work of M. Seaver et al in the International Journal of Mass Spectrometry and Ion Physics 1980, 34, pages 159 to 173 and reviewed by R. J. Cotter in Analytica Chimica Acta 1987, 195, pages 45 to 59.

Techniques for laser post-ionization of sputtered neutrals are generally categorized as using either resonant or non-resonant ionization. Resonant ionization occurs when the laser frequency is such that its associated photon energy matches the energy required to induce at least one electronic transition in the ionizing process. Several suitable resonance schemes are described by J. E. Parks et al in Thin Solid Films 1983, 108(2), pages 69 to 78, and the technique has been described variously by D. W. Beekman et al. in the International Journal of Mass Spectrometry and Ion Physics 1980, 34, pages 89 to 97; by N. Winograd et al in Chemical Physics Letters 1982, 88(6), pages 581 to 584, and in U.S. Pat. No. 4,442,354. In this technique the ionizing laser is tuned to correspond to a resonant transition and thus produces enhanced ionization with high selectivity of the ionized species in the presence of other substances for which the resonance condition is not satisfied. Such selectivity can be advantageous but requires some knowledge of the composition of a sample in advance of the analysis. By contrast, a technique based on non-resonant ionization as reported by C. H. Becker et al in U.S. Pat. No. 4,733,073 is inherently non-selective.

In Analytical Chemistry 1984, 56, pages 1671 to 1674, C. H. Becker et al give the major requirement of their non-resonant ionization technique as being a laser intensity high enough to achieve significant ionization probabilities. Non-resonant multi-photon ionization proceeds by a series of transitions to one or more virtual states which are not true eigenstates of the atom but between which transitions are possible in a very high light intensity as described by N. B. Delone in Soviet Physics Usp 1975, 18(3), pages 169 to 189. C. H. Becker et al have reported single photoionization studies of the surfaces of bulk polymers, and of molecular adsorbates, respectively in the Journal of Vacuum Science and Technology A 6(3), 1988, pages 936 to 940 and the Journal of the American Chemical Society 1988, 110, pages 2323 to 2324. Arrangements for the laser postionization of sputtered neutrals have also been reported in PCT Patent Applications Nos. W087/07762 and W088/06060 covering both resonant and non-resonant ionization processes.

A pervasive need exists to better understand the isotopic and elemental composition of complex (e.g., 3-D) macroscopic objects (ranging from Martian meteorites and fossilized dinosaur skeletons to epitaxially-grown novel materials and internationally-derived objects of uncertain but suspected-interesting origins or histories) on spatial scales of micrometers and within end-to-end object-analysis time-scales of minutes to days. The present invention provides a generally applicable solution to this analytic challenge.

SUMMARY OF THE INVENTION

It is an object of the present invention to provide a method and apparatus for sequentially disassembling an object of arbitrary shape, size and composition into a train of (usually very small) mass-packets and analyzing these mass-packets as they are removed from known locations on the parent-object for their chemical-elemental, molecular (fragment), or mass-isotopic composition.

Mass-packet removal from a parent-object is accomplished by exceedingly rapid ablation with a train of femtosecond-duration focused laser pulses, which heat the corresponding portion of the object's surface to temperatures far in excess of vaporization temperatures on time-scales very small compared to thermal conduction, thermal radiation or hydrodynamic relaxation processes. The super-heated mass-packets that then "jump off" of the surface are then readily analyzed by standard means for their composition.

The present materials-analysis invention is referred to herein as "Composition Analysis By Scanning Femtosecond Laser Ultraprobing" (CASFLU), and employs exceedingly short-duration laser pulses ($t_{1/2} \leq 10^{-12}$ seconds) of exceptionally high intensity ($I \geq 10^{13}$ W/cm$^2$) to heat a well-defined parcel of surface material to a large multiple of its vaporization temperature, raising the parcel into the temperature regime where it is relatively highly ionized (i.e., $T \geq 6{,}000$ K, or $kT \geq 0.5$ eV, where k is Boltzmann's constant), well before this material can expand-and-cool hydrodynamically or diffuse its heat into surrounding portions of the object being analyzed. These laser pulse-heating time-scales are typically 1,000 times shorter than the corresponding hydrodynamic times, and are even far shorter (by more than 100-fold) than the associated thermal conduction times for the imposed heat to be diffusively transported into surrounding material. Their use creates a sequence of (usually) tiny mass-parcels of superheated vapor at solid density, which then "jump off" the surface so irradiated in succession, each one leaving the surrounding surface essentially unperturbed, e.g., available for subsequent inspection, analysis, etc., without major perturbation or "pre-processing" by thermal or mechanical effects of the mass-removal.

This exceptionally "clean", side effects-free removal of mass-packets, which is unique to CASFLU relative to all the analytic approaches surveyed in the foregoing, permits the systematic, sequential disassembly of surfaces and volumes of objects of complex structure and highly-variable composition by repetitive, spatially-precise extraction of such mass-packets from exposed surfaces. Each such mass-parcel then may be readily composition-analyzed very soon after it commences to "jump off" the underlying surface, e.g., by a variety of spectrometric means of which (near-)optical- and mass-spectroscopy are major examples. Indeed, bringing nearly the entire mass-parcel to an electron temperature $\geq 0.5$ eV first-ionizes a substantial fraction (>1%) of all materials, i.e., gives an ion-to-atom fraction >$10^{-2}$, so that subsequent spectroscopy in the vibrational and electronic excitation spectra and in the mass spectrum usually doesn't require post-ionization, and thus is substantially facilitated.

DETAILED DESCRIPTION OF THE INVENTION

The invention is a method and apparatus for ultra-high resolution, 1, 2- and 3-D composition (isotopic, elemental and compound) analysis by mass- and electromagnetic-spectral analysis of the blow off plume-train induced by a scanned-and-focused sequence of ultra-short (e.g., femtosecond) laser-pulses. High-rate, general-purpose (isotopic, elemental and compound) composition analysis of 1-, 2- and 3-D macroscopic objects at sub-micron spatial resolution is thus enabled, e.g., for tracing origins and histories of peculiar objects (e.g., artifacts bearing embedded Special Nuclear Material). The invention enables high-rate, general-purpose, ultra-high spatial-resolution composition analysis of macroscopic objects of all types—a potentially very large analytic services market.

General Description

Composition Analysis by Scanning Femtosecond Laser Ultraprobing (CASFLU) directs relatively high-average-power trains of carefully-focused, sub-picosecond-duration laser pulses onto the surface of an object to be composition-analyzed, scanning the position of the focal spot over the surface in a controlled and known manner as a function of time. The laser intensity at the focal spot is made to be sufficiently high that the electron population in the proximate material is flash-heated to $\geq 0.5$ eV temperature within the duration of a single laser pulse, which is made to be substantially smaller than the thermal diffusion time of the material across the focal spot's radius (as well as the electron-ion coupling time in the local material, which is generally substantially longer than the thermal diffusion time across micron distance scales). A description of laser systems that provide ultrashort laser pulses for material processing is described in U.S. Pat. No. 5,720,894, incorporated herein by reference.

Figure 1:
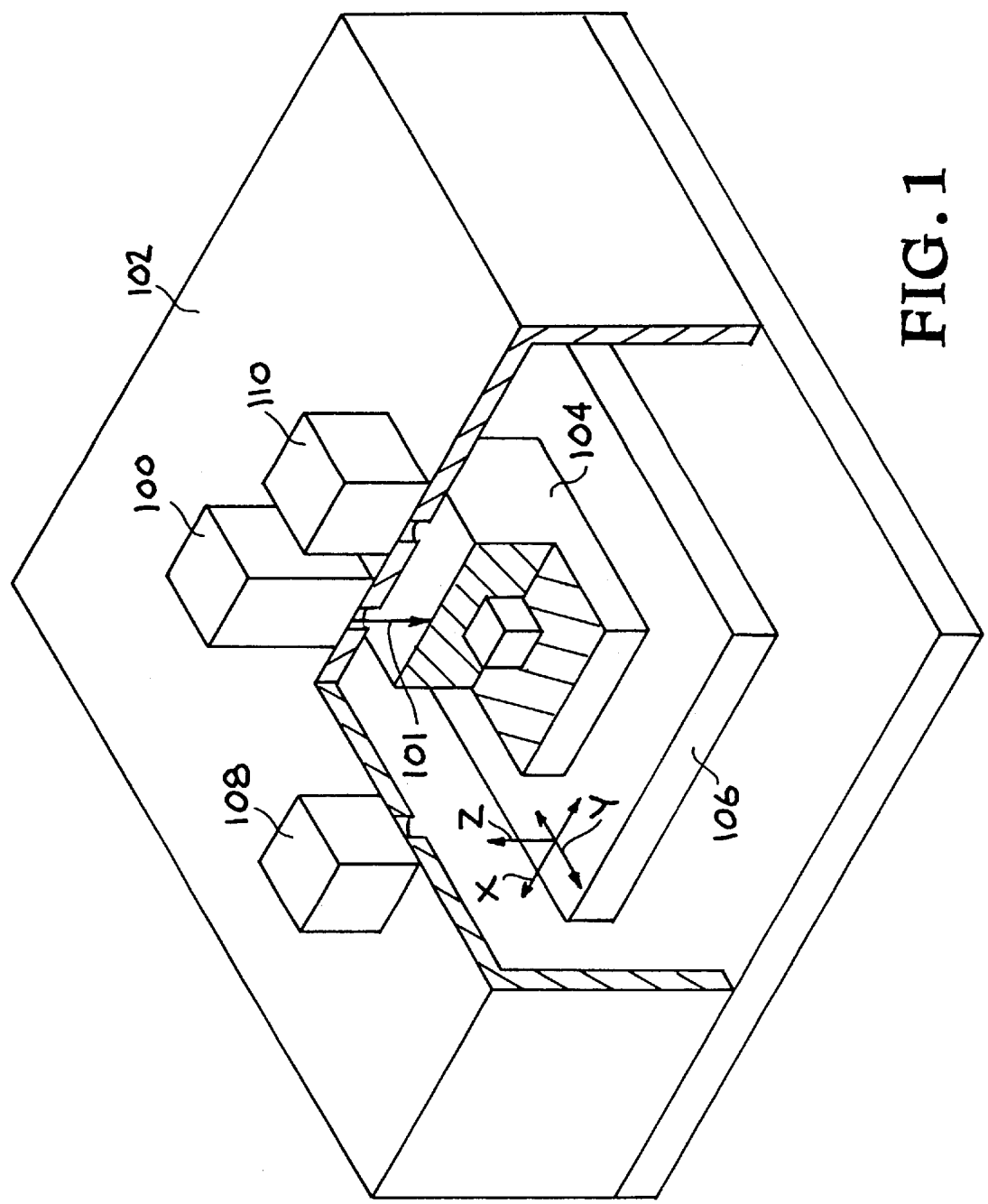
FIG. 1 illustrates an exemplary CASFLU system.

Toward the end of the laser pulse's (generally sub-) picosecond duration, the (electron) temperature of a very small portion of the material of the object being analyzed immediately under the focal spot becomes sufficiently high to eject at high speed the solid density-albeit-gasified material from the object's surface, moreover without significant disruption of the surrounding material (whose ionic temperature is still nearly ambient). This serves to present radiating (e.g., electronically and vibrationally-excited) ions, atoms, molecular fragments and intact molecules of the vaporized material to proximately positioned mass- and/or electromagnetic-spectrometric analytic device inputs, as well as to remove this mass-parcel in a predictable and controlled manner so as to expose underlying material to subsequent analytic probing (by the same or different means). Since each mass-parcel so evaporated will radiate brightly only for only a few hydrodynamic relaxation times (~1 nsec for a ~1 micron depth-or-diameter focal spot, whichever of these two dimensions is smaller), the use of suitable molecular/atomic/ionic fluorescence-detecting optics will permit the use of analytic pulse-trains of $\leq 100$ MHz rep-rate; if near-field mass spectrometric sampling of the evaporated material vapor is employed, analytic laser pulse-trains of $\leq 1$ MHz rep-rate are suitable. An exemplary CASFLU system is illustrated in FIG. 1. A laser system 100, generally corresponding to the laser system shown in FIG. 6 of the incorporated patent, provides a series of laser pulses 101 into enclosure 102 and onto a sample 104 in an inert gas provided by gas supply 108. A sample holder 106 operates to position the sample 104 for optimum material removal and composition analysis.

The focal spot of the laser may be made to be sub-micron in diameter, by use of suitably fast optics, and the laser beam focal spot may be scanned over the object's surface by motion of either (or both) the beam or the underlying object (the latter being accomplished by, e.g., 5- or 6-DOF high-precision positioning gear controlled by a dedicated computer). In applications in which analytic areas are large, it likely will be advantageous to employ small-scale/high-frequency optical beam deflection interfaced with large-scale/low-frequency object translation and/or rotation, in order to most practically scan the analyzing focal spot over the entire object, as it is ablated sequentially in picogram-scale mass-packets. Collateral imagery, e.g., possibly re-using the beam-focal optics, can serve to periodically document the site being CASFLU-analyzed. If desired, the focal spot diameter may be enlarged optically for removal of a larger area of the object's surface with each pulse, so as to provide a higher areal rate of analytic processing, the energy in each laser pulse being increased corresponding to the greater area irradiated by each pulse. (Approximately 10 kilojoules are required to remove-and-analyze a gram of most any material of analytic interest, so that a 1 cubic centimeter object of near-unit density may be completely analyzed with an efficiently-operated "small table-top" CASFLU system of 10 watt average power on a time-scale of ~20 minutes. A picosecond-duration laser pulse ablates a layer ~1 micron deep in most materials, so that a per-pulse fluence of ~1 joule per square centimeter is something of a practical upper bound for CASFLU utilization. Smaller ablation depths may be realized with shorter-duration laser pulses, and smaller focal spot diameters may be attained with faster optics and/or shorter wavelength laser radiation.)

CASFLU represents the first time that scanning micro-dissection and composition analysis of even macroscopic objects has been available via any technological approach that may be applied successively to a set of essentially unperturbed sample-surfaces, layer-stacked. All previous analytic technologies either thermally or mechanically "pre-process" iteratively- or continuously-analyzed surfaces, by depositing either heat or impulse in them in manners which degrades either the structure or the composition-resolution of the object being analyzed. With CASFLU, a freshly-exposed surface is effectively "unaware" that the immediately-overlying surface has been removed. CASFLU enables the use of as many as $10^8$ pulses-per-sec to be applied continuously for analytic durations of minutes to hours to an object which is desired to be analytically disassembled. Therefore, an object which is $10^{12}$ "matter pixels" in size may be disassembled in $10^4$ seconds using the CASFLU method and apparatus; CASFLU analysis of a typical semiconductor chip (~$10^{10}$ pixels in size) might take of the order of 2 minutes, as described in the foregoing and subsequently.

Specific Description

As required, detailed embodiments of the present invention are disclosed herein. However, it is to be understood that the disclosed embodiments are merely exemplary of the present invention that may be embodied in various systems. Therefore, specific details disclosed herein are not to be interpreted as limiting, but rather as a basis for the claims and as a representative basis for teaching one skilled in the art to variously practice the present invention.

As an applications example, high-precision reverse engineering of a very large, state-of-the-art integrated circuit (including the currently very challenging determination of dopant concentrations in buried layers) could be executed on a time-scale of 2 minutes, employing CASFLU in electronic fluorescence mode: a flying beam-spot focused to 0.25 micron diameter (e.g., employing F/0.6 optics and 0.34 micron wavelength laser light) would be scanned over the assumed 6 square centimeter chip-surface at a 100 MHz pulse rate, removing 100 million mass-packets of 0.25 micron diameter and 0.25 micron depth each second and thus requiring 1 second to thereby analyze the entire surface area of the chip. Over a two-minute interval, 100 such scans could remove-and-analyze the chip's surface down to a depth of 25 microns, thereby exposing the entire 3-D structure of the chip to high-sensitivity/high-rate spectroscopic analyses, moreover at a spatial resolution corresponding to a contemporary lithographic "minimum feature size" of 0.25 micron.

Figure 2:
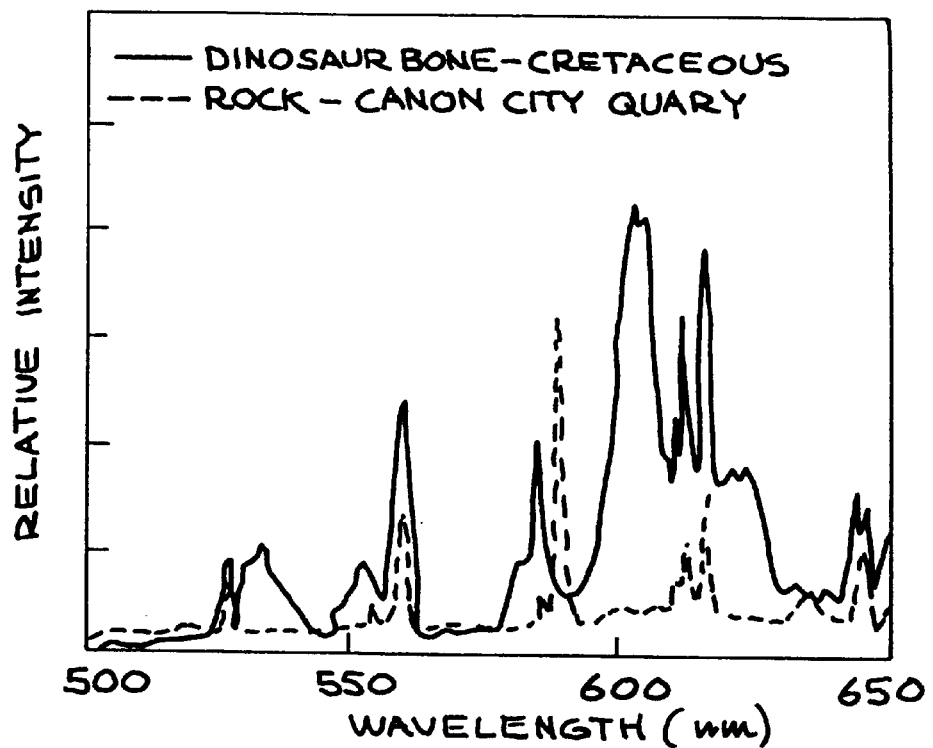
FIG. 2 demonstrates that fossilized bone can be readily distinguished via CASFLU from the similarly appearing rock in which it was embedded.
Figure 3:
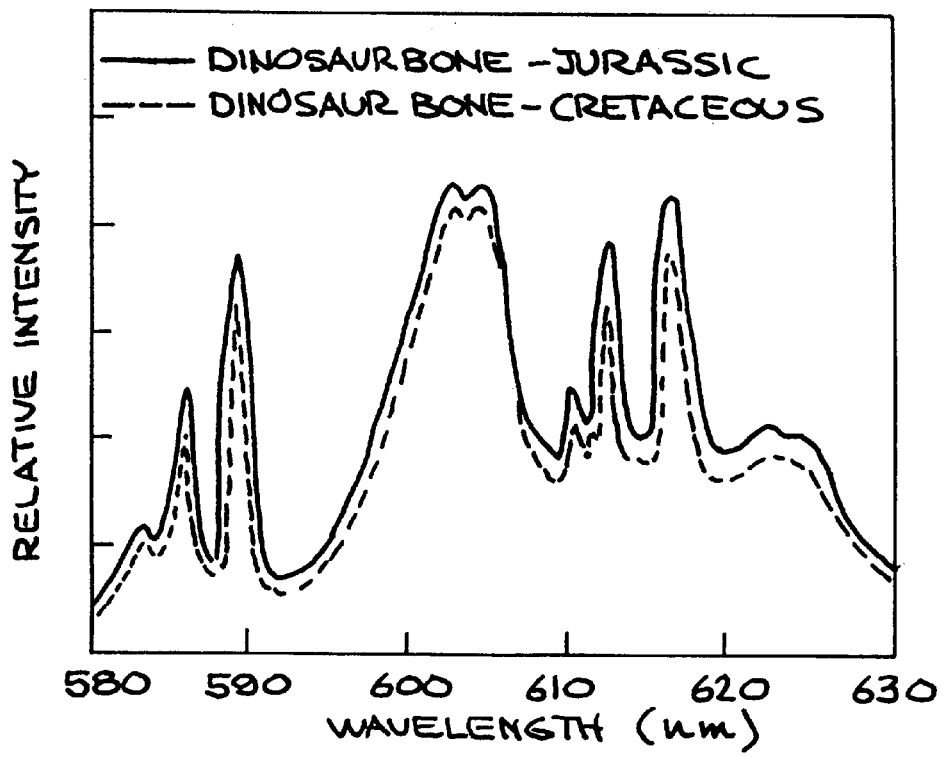
FIG. 3 compares the CASFLU signatures of dinosaur bones from the Jurassic period and the Cretaceous period.
Figure 4:
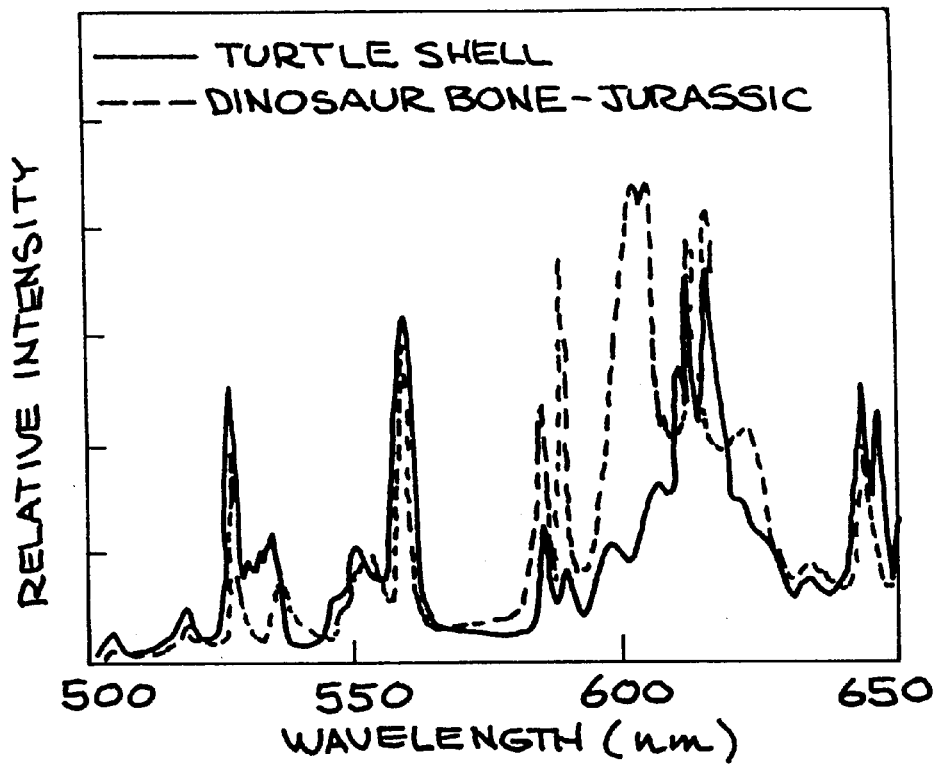
FIG. 4 compares the CASFLU signatures of turtle shell with dinosaur bones from the Jurassic period.
Figure 5:
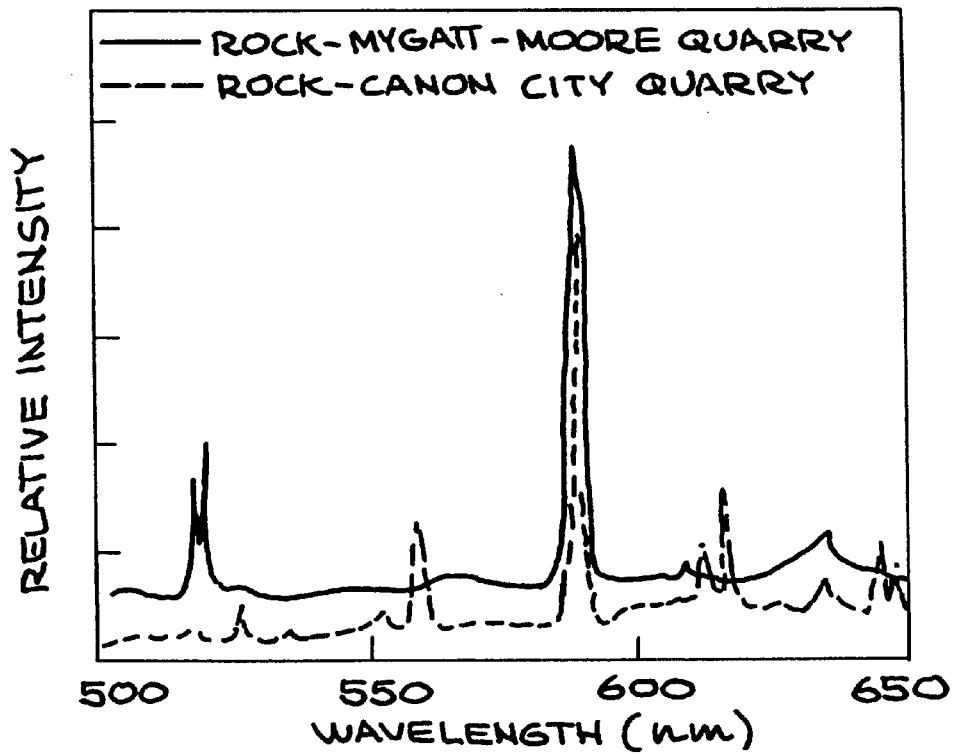
FIG. 5 compares the CASFLU signatures of rock taken from different quarries.

In a typical, non-exclusive, in-the-field exemplary use of CASFLU technology, a prototype CASFLU apparatus was employed to characterize the chemical elemental compositions of a series of one-dimensional tracks laid across a set of paleontological specimens, namely, fossilized bone and shell from several different large vertebrates (dinosaurs and turtles) of the Mesozoic Era. These employed laser pulses of 120 femtoseconds FWHM, focused to an intensity of ~$10^{13}$ Watts/cm$^2$, with planar surfaces of the specimens being swept under the focal spot and the optical emissions from the vaporized material being spectrally analyzed by a standard optical spectrometer. Typical results are shown in FIGS. 2–5. FIG. 2 demonstrates that fossilized bone can be readily CASFLU-distinguished (by its far greater concentration of chemical-element phosphorus, arising from the hydroxyapatite laid down by bone-forming processes when the animal was alive) from the similarly appearing rock in which it was embedded. FIGS. 3 and 4 compare the CASFLU results for a variety of fossilized bones whose ages varied by more than 80 million years. FIG. 3 compares the CASFLU signatures of dinosaur bones from the Jurassic period and the Cretaceous period. FIG. 4 compares CASFLU signatures of turtle shell and dinosaur bones from the Jurassic period. These results also demonstrated that fossilized chitin can be readily distinguished from fossilized bone (again, by its relative phosphorus content). FIG. 5 compares CASFLU signatures of rock taken from different quarries. These results were reported to the Society of Vertebrate Paleontology in a paper presented at its 1999 Annual Meeting (E. M. Campbell, et al., *J. Vertebrate Paleontology* 19(3), 35A, 1999).

Figure 6A:
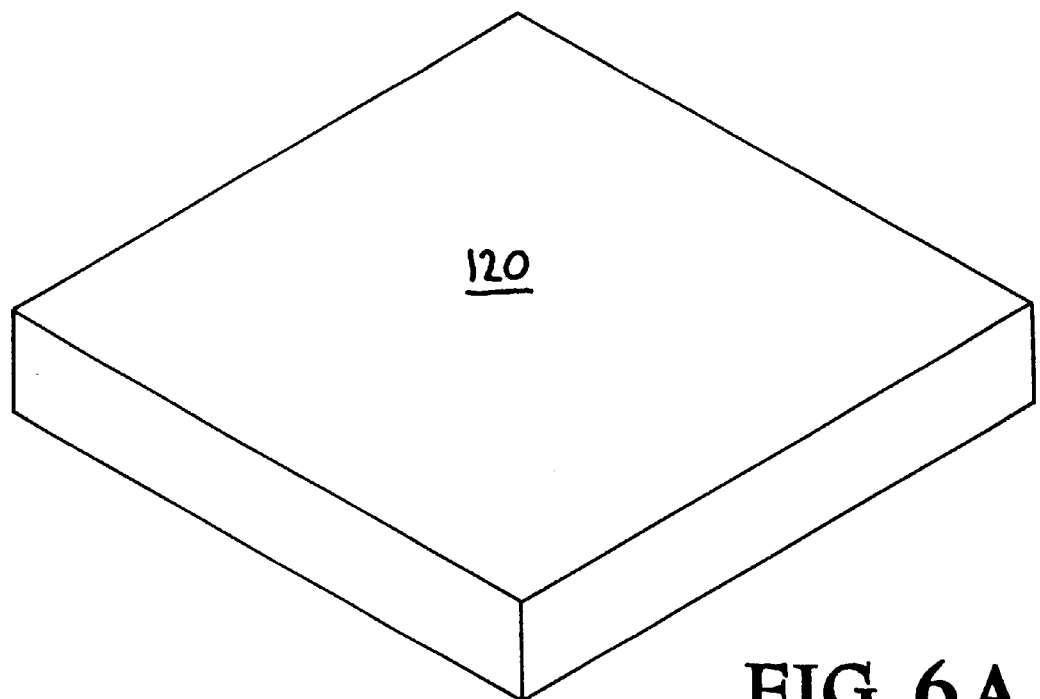
FIG. 6A shows the top side of an NTE 175 power transistor.
Figure 6B:
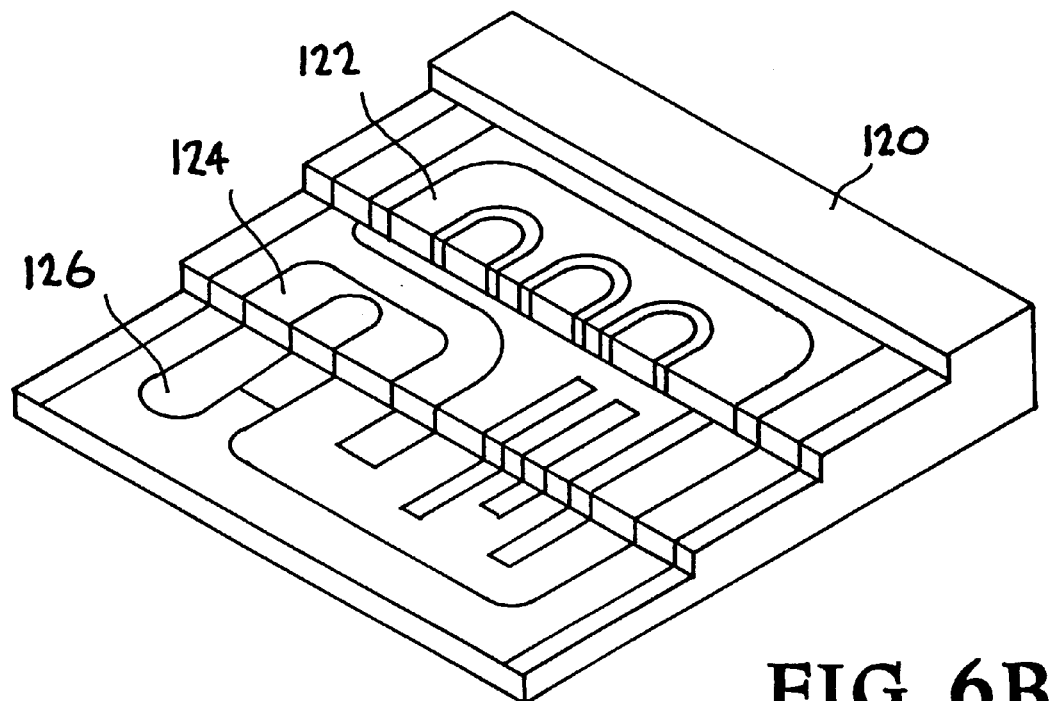
FIG. 6B illustrates the transistor of FIG. 6A with sections having different amounts of material removed for CASFLU composition analysis.

Another typical, non-exclusive, in-the-field exemplary use was the use of CASFLU technology to characterize the variable composition of an NTE 175 power transistor, by successively removing tiny mass-parcels from its surface in an x-y raster-scanning mode, analyzing the chemical-elemental composition of each parcel as it was removed by optical spectrometric means, the entire process being under the real-time control of a dedicated personal computer equipped with a digital data-acquisition module. After each such surface was so analyzed, the immediately underlying surface was then processed in the same manner and this entire process iterated, until only pure silicon from the semiconductor's substrate-material was found at any x-y location, indicating that the device had been completely analyzed. In this analytic run, the laser focal spot-diameter was 10 micrometers, and the focal spot intensity was made to be ~$10^{13}$ Watts/cm$^2$; the laser was typically operated at 1000 pulses per second, and the semiconductor was x-y raster-scanned under the focal spot at a lineal speed of 0.1 cm/second. FIG. 6A shows the top side of an NTE 175 power transistor. This portion is covered with silicon and is given reference number 120 in FIGS. 6A and B. FIG. 6B illustrates the transistor of FIG. 6A with sections 122, 124 and 126 each having a different amount of material removed for composition analysis.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A method of composition analysis, comprising:
   providing a sample of material to be analyzed;
   focusing a series of laser pulses to a focal spot on said sample, wherein each laser pulse of said series of laser pulses has a pulse duration that is less than 10 picoseconds and an intensity at said focal spot that is sufficiently high that the electron population in the irradiated portion of said sample at said focal spot is flash-heated to a temperature greater than 0.5 eV within the duration of each said laser pulse to produce vaporized material, wherein said vaporized material is ejected from said irradiated portion of the surface of said sample; and
   analyzing the composition of said vaporized material.

2. The method of claim 1, further comprising scanning the position of said focal spot over the surface of said sample in a controlled and known manner as a function of time.

3. The method of claim 1, wherein said pulse duration is made to be less than the smaller of the thermal diffusion time and the hydrodynamic relaxation time of said irradiated portion of said sample across the smaller of the radius of said focal spot or the heated-material depth within said focal spot.

4. The method of claim 1, wherein said pulse duration is made to be less than the thermal-diffusive relaxation time of said irradiated portion of said sample.

5. The method of claim 1, wherein said pulse duration is made to be less than the hydrodynamic relaxation time of said irradiated portion of said sample.

6. The method of claim 3, wherein said laser pulse duration is made to be less than the electron-ion coupling time of said irradiated portion of said sample.

7. The method of claim 1, wherein the step of analyzing the composition of said vaporized material comprises injecting a sample of said vaporized material into a mass spectrometer.

8. The method of claim 1, wherein the step of analyzing the composition of said vaporized material comprises injecting a sample of said vaporized material into a spectrometer sensitive to electromagnetic radiation having a wave-frequency within a range from $10^{13}$ to $10^{16}$ Hertz.

9. The method of claim 1, wherein each laser pulse of said series of laser pulses has an intensity that is greater than or equal to $10^{13}$ W/cm$^2$.

10. The method of claim 1, wherein the step of analyzing the composition is carried out with molecular/atomic/ionic fluorescence-detecting optics, wherein said series of laser pulses is provided at a repetition rate$\leq$100 MHz.

11. The method of claim 1, wherein the step of analyzing the composition is carried out with near-field mass spectrometric sampling, wherein said series of laser pulses is provided at a repetition rate$\leq$1 MHz.

12. The method of claim 1, wherein the focal spot diameter of said focused laser pulses is enlarged optically for removal of a larger area of the object's surface with each pulse, to provide a higher rate of analytic processing, wherein the energy in each laser pulse is increased corresponding to the greater area irradiated by each pulse.

13. A method of composition analysis, comprising:
   directing a series of focused laser pulses onto a surface of an object to be composition-analyzed, wherein each laser pulse of said series of focused laser pulses comprises a pulse duration that is less than 10 picoseconds and an intensity at said focal spot that is sufficiently high that the electron population in the material of said sample at said focal spot is heated to a temperature greater than 0.5 eV within the duration of each said laser pulse;
   scanning the position of said focused laser pulses over said surface of said object in a controlled and known manner as a function of time, wherein a vaporized portion of said object immediately under said focused pulses becomes sufficiently heated to eject at high speed from said object in an initially solid-density gasified phase without significant disruption of the surrounding material; and
   analyzing the composition of said vaporized portion of said object.

14. The method of claim 13, wherein the step of analyzing the composition is carried out with molecular/atomic/ionic fluorescence-detecting optics, wherein said series of laser pulses is provided at a repetition rate$\leq$100 MHz.

15. The method of claim 13, wherein the step of analyzing the composition is carried out with near-field mass spectrometric sampling, wherein said series of laser pulses is provided at a repetition rate$\leq$1 MHz.

16. The method of claim 13, wherein the focal spot diameter of said focused laser pulses is enlarged optically for removal of a larger area of the object's surface with each pulse, so as to provide a higher mass-rate of analytic processing, wherein the energy in each laser pulse is increased corresponding to the greater area irradiated by each pulse.

17. A system for composition analysis, comprising:
   a sample holding-and-positioning system for holding-and-positioning a sample to be analyzed;
   a laser system for providing and focusing a series of laser pulses to a focal spot on said sample, wherein each laser pulse of said series of laser pulses has a pulse duration that is less than 10 picoseconds and an intensity at said focal spot that is sufficiently high that the electron population in said irradiated portion of said sample at said focal spot is flash-heated to a temperature greater than 0.5 eV within the duration of each said laser pulse to produce vaporized material, wherein said vaporized material is ejected from the surface of said sample; and means for analyzing the composition of said vaporized material.

18. The system of claim 17, further comprising means for scanning the position of said focal spot over the surface of said sample in a controlled and known manner as a function of time.

19. The system of claim 17, wherein said means for analyzing the composition of said vaporized material comprises a mass spectrometer.

20. The system of claim 17, wherein said means for analyzing the composition of said vaporized material comprises a spectrometer sensitive to electromagnetic radiation having a wave-frequency within a range from $10^{13}$ to $10^{16}$ Hertz.

21. The system of claim 17, wherein said means for analyzing the composition of said vaporized material comprises molecular/atomic/ionic fluorescence-detecting optics.

22. The system of claim 17, wherein said means for analyzing the composition of said vaporized material comprises a near-field mass spectrometer.

23. The system of claim 17, wherein said laser system comprises means for enlarging the focal spot diameter of said focused laser pulses for ablative removal of a larger area of the object's surface with each pulse, to provide a higher mass-rate of analytic processing, wherein the energy in each laser pulse is increased corresponding to the greater area irradiated by each pulse.

24. A system for composition analysis, comprising:

means for directing a series of focused laser pulses onto a surface of an object to be composition-analyzed, wherein each laser pulse of said series of focused laser pulses comprises a pulse duration that is less than 10 picoseconds and an intensity at said focal spot that is sufficiently high that the electron population in said irradiated portion of said sample at said focal spot is heated to a temperature greater than 0.5 eV within the duration of each said laser pulse;

means for scanning the focused position of said laser pulses over said surface of said object in a controlled and known manner as a function of time, wherein a portion of said object immediately under said focused pulses becomes sufficiently heated to eject at high speed from said object in an initially solid-density gasified phase without significant disruption of the surrounding material; and means for analyzing the composition of said vaporized portion of said object.

* * * * *